United States Patent [19]

Micetich et al.

[11] Patent Number: 4,496,484
[45] Date of Patent: Jan. 29, 1985

[54] PENICILLIN DERIVATIVES

[75] Inventors: Ronald G. Micetich, Sherwood Park, Canada; Shigeru Yamabe, Kobe, Japan; Shoji Hirata, Matsudo, Japan; Naobumi Ishida, Tokushima, Japan

[73] Assignee: Taiho Pharmaceutical Company, Limited, Tokyo, Japan

[21] Appl. No.: 487,357

[22] Filed: Apr. 22, 1983

[51] Int. Cl.³ ............... C07D 499/00; A61K 31/425
[52] U.S. Cl. .................... 260/245.2 R; 424/270; 260/239 A; 260/245.2 T
[58] Field of Search ............ 260/245.2 R, 239.1; 424/270, 271

[56] References Cited

U.S. PATENT DOCUMENTS

| | | | |
|---|---|---|---|
| 4,009,159 | 2/1977 | Kamiya et al. | 260/239.1 |
| 4,036,847 | 7/1977 | Kamiya et al. | 260/306.7 C |
| 4,071,527 | 1/1978 | Kamiya et al. | 260/306.5 |
| 4,234,579 | 11/1980 | Barth | 424/246 |
| 4,340,539 | 7/1982 | Gottstein | 260/245.2 R |

FOREIGN PATENT DOCUMENTS 56-104886   8/1981   Japan .

OTHER PUBLICATIONS

Gottstein et al., J. Med. Chem., 1981, vol. 24, 1531–1534.

Primary Examiner—Nicholas S. Rizzo
Attorney, Agent, or Firm—Robert B. Murray; Fred S. Whisenhunt; Gerald J. Ferguson, Jr.

[57] ABSTRACT

This invention provides a penicillin derivative of the formula and a salt thereof

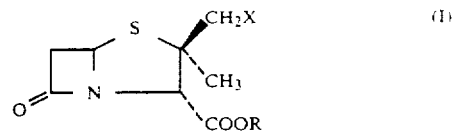

wherein X represents chlorine atom or bromine atom and R represents hydrogen atom or penicillin carboxy-protecting radical, and a process for preparing the derivative of the formula (I) and a salt thereof by reacting a compound of the formula

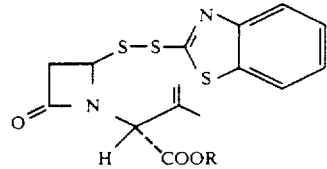

wherein R is as defined above with a chlorinating reagent or brominating reagent and, when required, forming a salt thereof.

8 Claims, No Drawings

PENICILLIN DERIVATIVES

This invention relates to penicillin derivatives usable as a starting material for preparing derivatives of 2β-(substituted methyl)-2α-methylpenam-3α-carboxylic acid having β-lactamase inhibitory properties and to a process for preparing the same.

Of the commercially available antibiotics, β-lactam type antibiotics having a β-lactam ring, namely penicillins and cephalosporins, are best known and frequently used. Although widely used as useful chemotherapeutic drugs, the β-lactam type antibiotics can not achieve satisfactory effects against some types of microorganisms because of resistance of the microorganism to the β-lactam type antibiotics. The resistance thereof are usually attributable to β-lactamase produced by the microorganism. The β-lactamase is an enzyme which acts to cleave the β-lactam ring of the β-lactam type antibiotic, thereby causing the antibiotic to lose its antimicrobial activity. For this reason, the action of β-lactamase must be eliminated or inhibited so as to enable the β-lactam type antibiotic to produce satisfactory effects. The elimination or inhibition of the β-lactamase activity can be achieved by β-lactamase inhibitors, which are used conjointly with the β-lactam type antibiotic to increase the antimicrobial activity of the antibiotic. In recent years, research on β-lactamase inhibitors has been extensively conducted. The β-lactamase inhibitors under investigation include derivatives of 2β-(substituted methyl)-2α-methylpenam-3α-carboxylic acid 1,1-dioxide.

An example of the derivatives is described in Japanese Unexamined Patent Publication No. 104886/1981 which discloses 2β-chloromethyl-2α-methylpenam-3α-carboxylic acid 1,1-dioxide having β-lactamase inhibiting activity and represented by the formula

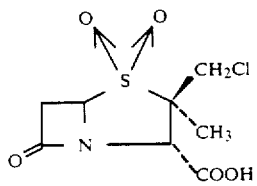

The following two compounds of the formulae (III) and (IV) also have a high β-lactamase inhibitory action.

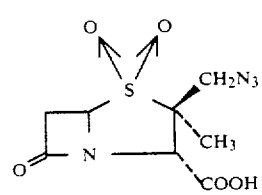

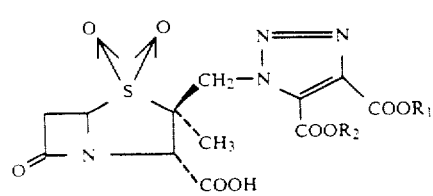

wherein $R_1$ and $R_2$ represent lower alkyl radical.

We found that the compounds of the formulae (III) and (IV) can be readily prepared by using as a starting material a penicillin derivative of the following formula (I) or a salt thereof

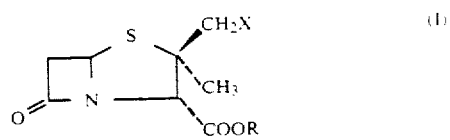

wherein X represents chlorine atom or bromine atom, and R represents hydrogen atom or penicillin carboxy-protecting radical. We also found that the compound of the formula (I) can be used as an excellent starting material for synthesizing the compound of the formula (II). The present invention was accomplished based on these novel findings.

The penicillin derivatives of the present invention are represented by the formula

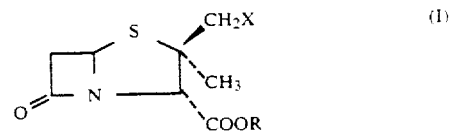

wherein X and R are as defined above.

Illustrative salts of the derivatives having the formula (I) which are prepared according to the present invention include salts of alkali metals such as sodium, potassium and lithium; salts of alkaline earth metals such as calcium and magnesium; salts of organic amines such as cyclohexylamine, trimethylamine and diethanolamine; salts of basic amino acids such as alginine and lysine; ammonium salts; etc.

Examples of the penicillin carboxy-protecting radicals represented by R in the formula (I) include known radicals. Representative radicals are set forth in Japanese Unexamined Publication No. 81380/1974 and H. E. Flynn, "Cephalosporin And Penicillins Chemistry And Biology" (1972, Academic Press). Specific examples of the penicillin carboxy-protecting radicals are methyl, ethyl, propyl, tert-butyl, pentyl, hexyl and like lower alkyl groups; iodomethyl, 2,2-dibromoethyl, 2,2,2-trichloroethyl and like halogenated lower alkyl groups substituted with 1 to 3 halogen atoms such as Cl, Br or I; benzyl, p-methoxybenzyl, o-nitrobenzyl, p-nitrobenzyl, diphenylmethyl and like methyl group substituted with 1 to 3 phenyl groups which may be unsubstituted or may be substituted with methoxy or nitro on the phenyl ring; methoxymethyl, ethoxymethyl, n-propyloxymethyl, iso-propyloxymethyl, n-butoxymethyl, iso-butoxymethyl and like lower alkoxymethyl groups; acetoxymethyl, propionyloxymethyl, n-butyryloxymethyl, iso-butyryloxymethyl, pivalyloxymethyl, 1-acetoxyethyl, 1-pivalyloxyethyl, 1-pivalyloxypropyl, 1-propionyloxybutyl and like lower alkyl-carbonyloxy-lower alkyl; cyclopentylcarbonyloxymethyl, cyclohexylcarbonyloxymethyl and like ($C_5$–$C_7$ cycloalkyl)-carbonyloxy-lower alkyl groups; benzylcarbonyloxymethyl and like benzylcarbonyloxy-lower alkyl groups; benzoyloxymethyl, benzoyloxyethyl and like benzoyloxy-lower alkyl groups, etc. The term "lower" used in conjunction with "alkyl" or "alkoxy" is intended to indicate that each alkyl or alkoxy portion therein can contain 1 to 6 carbon atoms. The alkyl or alkoxy groupings can be straight- or branched-chain groups. Other examples of the penicillin carboxy-protecting radicals include phthalidyl, tetrahydropyranyl, 5-oxo-2-tetrahydrofuranyl, dimethylaminoethyl, dimethylchlorosilyl, trichlorosilyl, etc.

The compounds of the present invention are (1) 2β-chloromethyl-2α-methylpenam-3α-carboxylic acid, (2) 2β-bromomethyl-2α-methylpenam-3α-carboxylic acid and the foregoing salts thereof and the aforesaid esters thereof.

The penicillin derivatives of the present invention having the formula (I) are prepared by reacting a compound represented by the formula

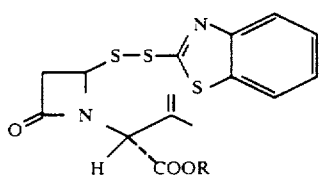

(V)

wherein R is as defined above with a chlorinating reagent or brominating reagent.

The compounds of the formula (V) are known and are prepared by the process disclosed in Japanese Unexamined Patent Publication No. 130981/1980.

Typical chlorinating reagents are hydrogen chloride, cupric chloride, mercuric chloride, etc. Typical brominating reagents are hydrogen bromide, cupric bromide, mercuric bromide, etc. The reaction according to this invention is usually conducted in a solvent. Usable as the solvent is any of solvents which do not affect the reaction, such as chloroform, methylene chloride, carbon tetrachloride and like halogenated hydrocarbons, acetone, acetonitrile, methanol, ethanol, acetic acid, etc.

The reaction temperature is suitably determined according to the type of the reagent to be used, and generally ranges from about −40° C. to room temperature. For example, when cupric chloride or cupric bromide is used, the reaction temperature ranges from −20° C. to room temperature.

In the reaction between the compound of the formula (V) and the chlorinating reagent or the brominating reagent, at least one mole of the reagent is used per mole of the compound of the formula (V), and preferably they are employed in equimolecular amounts.

The compounds of the formula (I) wherein R represents a hydrogen atom can alternatively be prepared by eliminating the carboxy-protecting group of the esters of the formula (I) wherein R represents the carboxy-protecting radical. The method of eliminating the carboxy-protecting radical depends upon the kind of carboxy-protecting radical. Generally, however, such elimination can be achieved by either reducing the ester or treating the ester with an acid.

The reduction can be conducted by treating the ester of the formula (I) with a mixture of (a) zinc, zinc-amalgam or like metal and/or chromium chloride, chromium acetate or like chromium salt and (b) formic acid, acetic acid or like acid. Alternatively, the reduction can be conducted with use of a catalyst in hydrogen atmosphere in a solvent. Examples of the catalysts are platinum, platinum oxide, palladium, palladium oxide, palladium-barium sulfate, palladium-calcium carbonate, palladium-carbon, nickel oxide, Raney-nickel, etc. The solvents are not particularly limited so far as they do not affect the reaction, and include methanol, ethanol and like alcohols; tetrahydrofuran, dioxane and like ethers; ethyl acetate and like esters; acetic acid and like fatty acids; and a mixture of these organic solvents and water.

The acids useful for eliminating the carboxy-protecting group of the ester of the formula (I) are formic acid, acetic acid and like lower fatty acids; trichloroacetic acid, trifluoroacetic acid and like trihalogenated acetic acids; hydrochloric acid, hydrofluoric acid and like hydrohalogenic acids; p-toluene-sulfonic acid, trifluoromethane-sulfonic acid and like organic sulfonic acids; and a mixture of these. In this reaction, when the acid used is in a liquid state and acts also as a solvent, it is not necessary to use other solvents. However, dimethylformamide, dichloromethane, chloroform, tetrahydrofuran, acetone and like solvents which do not affect the reaction may be used.

Salts of the penicillin derivatives of the formula (I) can be prepared by reacting the free penicillin carboxylic acid with an inorganic or organic base. Examples of the inorganic base are sodium hydrogencarbonate, sodium carbonate, sodium hydroxide, potassium hydrogencarbonate, potassium carbonate, potassium hydroxide, lithium carbonate, lithium hydroxide; calcium carbonate, calcium hydroxide, magnesium carbonate, magnesium hydroxide, etc. Examples of the organic amines are cyclohexylamine, trimethylamine, diethanolamine, basic amino acids, ammonia, etc. Amount of the inorganic or organic base to be used is about 0.5 to about 2 moles, per mole of the free penicillin carboxylic acid. The reaction is conducted in a solvent. Useful solvents are not particularly limited so far as they do not affect the reaction, and include methanol, ethanol and like alcohols; N,N-dimethylformamide, dimethylsulfoxide and like aprotic polar organic solvents, etc.

The salts may also be prepared by a salt exchange reaction in which the free penicillin carboxylic acid is reacted with a salt of a straight-chain or branched-chain fatty acid in a solvent. The solvents are not particularly limited so far as they are capable of precipitating the resulting salt of the penicillin carboxylic acid, and include ethyl acetate, butanol, etc.

Alternatively, the salts can be prepared from the ester of the penicillin carboxylic acid. First, the carboxy-protecting radical of the ester is eliminated in a solvent which contains the foregoing inorganic base, thereby to concurrently form the salt. Useful solvents are those which do not affect the reaction, and include tetrahydrofuran, dioxane and like ethers, ethyl acetate and like acetates; and a mixture of these and water.

The compounds thus obtained are purified by conventional methods such as recrystallization, extraction, column chromatography, etc.

The present invention will be described below in more detail with reference to reference examples and examples. Reference examples describe the process for preparing the compound of the formula (II), (III) or (IV) by using the compound of the formula (I) of the present invention.

REFERENCE EXAMPLE 1

Preparation of benzhydryl ester of 2β-chloromethyl-2α-methylpenam-3α-carboxylic acid 1,1-dioxide Potassium permanganate (1.2 g) was added under stirring to a solution of benzhydryl ester of 2β- chloromethyl-2α-methylpenam-3α-carboxylic acid (1.40 g) in a mixture of acetic acid (60 ml) and water (8 ml). The reaction mixture was agitated at room temperature for 3 hours, and then ice and water (100 ml) were added to produce a white precipitate which was filtered off. The precipitate was washed with ice water, and was dissolved in ethyl acetate. The solution was dried over magnesium sulfate, and the solvent was removed by distillation. There was obtained 1.1 g of benzhydryl ester of 2β-chloromethyl-2α-methylpenam-3α-carboxylic acid, 1,1-dioxide.

Infrared absorption spectrum (nujol). $\nu_{max}$ (cm$^{-1}$): 1800, 1750.

Nuclear magnetic resonance spectrum (CDCl$_3$) δ(ppm): 1.25 (3H, s), 3.43 (2H, d).

REFERENCE EXAMPLE 2

(A) Preparation of benzhydryl ester of 2β-azidomethyl-2α-methylpenam-3α-carboxylic acid An aqueous solution (25 ml) containing 2.38 g of sodium azide was added to a solution of benzhydryl ester of 2β-chloromethyl-2α-methylpenam-3α-carboxylic acid (2.44 g) in dimethylformamide (100 ml). The mixture was stirred at room temperature for 4 hours. The reaction mixture was poured into water and the resulting mixture was extracted with ether. The ether layer was washed with water and concentrated, giving 2.2 g of oil in 89% yield.

Infrared absorption spectrum (nujol). $\nu_{max}$ (cm$^{-1}$): 2120, 1812, 1765.

Nuclear magnetic resonance spectrum (CDCl$_3$). δ(ppm): 1.30 (3H, s), 3.25 (2H, m), 3.42 (1H, d), 3.63 (1H, d), 4.75 (1H, s), 4.76 (1H, m), 7.00 (1H, s), 7.40 (10H, s).

(B) Preparation of benzhydryl ester of 2β-azidomethyl-2α-methylpenam-3α-carboxylic acid 1,1-dioxide Benzhydryl ester of 2β-azidomethyl-2α-methylpenam-3α-carboxylic acid (2.22 g) and potassium permanganate (1.9 g) were added to a mixture of acetic acid (75 ml) and water (12 ml). The mixture was stirred at room temperature for 4 hours and ice water was added to produce a precipitate which was filtered off. The precipitate was washed with water and dissolved in ether. The solution was washed with an aqueous solution of sodium hydrogen carbonate and concentrated. There was obtained 1.49 g of the contemplated product in 62.2% yield.

Infrared absorption spectrum (nujol). $\nu_{max}$ (cm$^{-1}$): 2120, 1812, 1765.

Nuclear magnetic resonance spectrum (CDCl$_3$) δ(ppm): 1.18 (3H, s), 3.50 (2H, d), 3.72 (1H, d), 3.93 (1H, d), 4.60 (1H, m), 4.65 (1H, s), 7.00 (1H, s), 7.36 (10H, s).

REFERENCE EXAMPLE 3

Preparation of benzhydryl ester of 2β-(4,5-dimethoxycarbonyl-1,2,3-triazol-1-yl)methyl-2α-methylpenam-3α-carboxylic acid 1,1-dioxide Benzhydryl ester of 2β-azidomethyl-2α-methylpenam-3α-carboxylic acid 1,1-dioxide (0.870 g) and dimethyl acetylene-dicarboxylate (0.618 g) were refluxed with stirring in 15 ml of benzene in nitrogen atmosphere for 18 hours. The solvent was removed by distillation and the residue was eluted by silica gel column chromatography (ethyl acetate/chloroform = 1:3). There was obtained 0.495 g of contemplated product as light yellow crystals in 44% yield which melts at 75° to 77° C.

Infrared absorption spectrum (KBr). $\nu_{max}$ (cm$^{-1}$): 1800, 1735.

Nuclear magnetic resonance spectrum (CDCl$_3$). δ(ppm): 1.20 (3H, s), 3.48 (2H, t), 3.97 (3H, s), 3.98 (3H, s), 4.59 (1H, m), 4.95 (1H, s), 5.26 (2H, s), 6.97 (1H, s), 7.36 (10H, s).

EXAMPLE 1

Preparation of benzhydryl ester of 2β-chloromethyl-2α-methylpenam-3α-carboxylic acid A solution of benzhydryl 2-oxo-4-(benzothiazol-2-yl)dithio-α-isopropenyl-1-azetidine acetate (2.1 g) and cupric chloride (0.5 g) in methylene chloride (100 ml) was stirred at room temperature for 5 hours. The reaction mixture was filtered, and the filtrate was washed with water, dried over magnesium sulfate and concentrated to provide a yellow oil. The oil was subjected to chromatography on a silica gel column, producing 1.4 g of benzhydryl ester of 2β-chloromethyl-2α-methylpenam-3α-carboxylic acid from a fraction of methylene chloride.

Infrared absorption spectrum (Nujol). $\nu_{max}$ (cm$^{-1}$): 1800, 1750.

Nuclear magnetic resonance spectrum (CDCl$_3$). δ(ppm): 1.42 (3H, s), 3.07 (1H, dd), 3.58 (1H, dd), 3.63 (2H, s), 5.19 (1H, s), 5.42 (1H, dd), 7.0 (1H, s), 7.4 (10H, m).

EXAMPLE 2

Following the general procedure of Example 1 and substituting therein the appropriate reactants affords p-nitrobenzyl ester of 2β-chloromethyl-2α-methylpenam-3α-carboxylic acid.

Melting point: 103° to 104° C. (white crystals).

Infrared absorption spectrum (KBr). $\nu_{max}$ (cm$^{-1}$): 1780, 1750.

Nuclear magnetic resonance spectrum (CDCl$_3$). δ(ppm): 1.49 (3H, s), 3.14 (1H, dd), 3.65 (1H, dd), 3.62 (2H, s), 5.12 (1H, s), 5.30 (2H, bd), 5.3-5.5 (1H, m), 7.5-7.7 (2H, m), 8.1-8.4 (2H, m).

EXAMPLE 3

Preparation of benzyhydryl ester of 2β-bromomethyl-2α-methylpenam-3α-carboxylic acid A solution of benzhydryl 2-oxo-4-(benzothiazol-2-yl)dithio-α-isopropenyl-1-azetidine acetate (2.8 g) and cupric bromide (1.28 g) in methylene chloride (60 ml) at −10° C. for 4 hours. The reaction mixture was filtered, and the residue was washed with methylene chloride. The methylene chloride solutions were combined, and the mixture was washed with a solution of sodium hydrogen carbonate and further with water, and dried over magnesium sulfate. The resulting solution was concentrated to provide a light yellow oil. The oil was subjected to column chromatography, producing 2.2 g of contemplated product from a fraction of methylene chloride.

Infrared absorption spectrum (KBr). $\nu_{max}$ (cm$^{-1}$): 1780, 1730.

Nuclear magnetic resonance spectrum (CDCl$_3$). δ(ppm): 1.40 (3H, s), 2.9-3.3 (1H, m), 3.4-3.8 (1H, m), 3.60 (2H, s), 5.25 (1H, s), 5.3-5.5 (1H, m), 6.95 (1H, s), 7.1-7.8 (10H, m).

We claim:

1. A penicillin derivative represented by the following formula and alkali metal, alkaline earth metal, cyclohexylamine, trimethylamine, diethanolamine, alginine, lysine or ammonium salts thereof

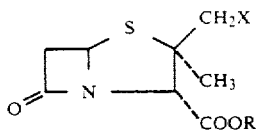

wherein X represents chlorine atom or bromine atom, and R represents hydrogen atom, $C_{1-6}$ alkyl, $C_{1-6}$ alkyl substituted with 1 to 3 halogen atoms, methyl group substituted with 1 to 3 phenyl groups which may optionally be substituted with methoxy or nitro on the phenyl ring, $C_{1-6}$ alkoxymethyl, $C_{1-6}$ alkylcarbonyloxy-$C_{1-6}$ alkyl, ($C_{5-7}$ cycloalkyl)carbonyloxy-$C_{1-6}$ alkyl, benzylcarbonyloxy-$C_{1-6}$ alkyl, benzoyloxy-$C_{1-6}$ alkyl, phthalidyl, tetahydropyranyl, 5-oxo-2-tetrahydrofuranyl, dimethylaminoethyl, dimethylchlorosilyl or trichlorosilyl.

2. A compound as defined in claim 1 wherein methyl group substituted with 1 to 3 phenyl groups which may optionally be substituted with methoxy or nitro on the phenyl ring represented by R is benzyl, p-methoxybenzyl, p-nitrobenzyl, o-nitrobenzyl or diphenylmethyl.

3. A compound as defined in claim 1 wherein X is a chlorine atom.

4. A compound as defined in claim 1 which is 2β-chloromethyl-2α-methylpenam-3α-carboxylic acid.

5. A compound as defined in claim 1 which is 2β-chloromethyl-2α-methylpenam-3α-carboxylic acid p-nitrobenzyl ester.

6. A compound as defined in claim 1 which is 2β-chloromethyl-2α-methylpenam-3α-carboxylic acid diphenylmethyl ester.

7. A compound as defined in claim 1 which is 2β-bromomethyl-2α-methylpenam-3α-carboxylic acid.

8. A compound as defined in claim 1 which is 2β-bromomethyl-2α-methylpenam-3α-carboxylic acid diphenylmethyl ester.

* * * * *